US00PP14620P29

(12) United States Plant Patent
Vandenberg

(10) Patent No.: US PP14,620 P2
(45) Date of Patent: Mar. 23, 2004

(54) CHRYSANTHEMUM PLANT NAMED "TRUE"

(50) Latin Name: *Chrysanthemum×morifolium*
Varietal Denomination: True

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/452,063

(22) Filed: Jun. 2, 2003

(51) Int. Cl.[7] ..... A01H 5/00
(52) U.S. Cl. ..... Plt./293
(58) Field of Search ..... Plt./293

*Primary Examiner*—Anne Marie Grunberg
(74) *Attorney, Agent, or Firm*—C. A. Whealy

(57) ABSTRACT

A distinct cultivar of Chrysanthemum plant named 'True', characterized by its upright plant habit; freely flowering habit; decorative-type inflorescences that are about 6.9 cm in diameter; attractive dark red purple-colored ray florets; response time about 64 days; dark green foliage; strong and thick flowering stems and peduncles; and good postproduction longevity with inflorescences and foliage maintaining good substance and color for about 14 to 18 days in an interior environment.

2 Drawing Sheets

Botanical classification/cultivar designation: *Chrysanthemum×morifolium* cultivar True.

BACKGROUND OF THE INVENTION

The present invention relates to a new and distinct cultivar of Chrysanthemum plant, botanically known as *Chrysanthemum×morifolium* and hereinafter referred to by the name 'True'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross-pollination made by the Inventor in March, 1996, in Salinas, Calif., of a proprietary *Chrysanthemum×morifolium* seedling selection identified as code number C911, not patented, as the female, or seed, parent with a proprietary *Chrysanthemum×morifolium* seedling selection identified as D458, not patented, as the male, or pollen, parent.

The cultivar True was discovered and selected by the Inventor as a flowering plant within the progeny of the stated cross-pollination in a controlled environment in Alva, Fla., in March, 1997. The selection of this plant was based on its desirable inflorescence color and good form and substance.

Asexual reproduction of the new Chrysanthemum by terminal cuttings taken in a controlled environment in Alva, Fla. since June, 1997, has shown that the unique features of this new Chrysanthemum are stable and reproduced true to type in successive generations.

SUMMARY OF THE INVENTION

Plants of the cultivar True have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'True'. These characteristics in combination distinguish 'True' as a new and distinct cultivar:

1. Upright cut Chrysanthemum that is usually grown as a natural spray.
2. Freely flowering habit, about six or seven inflorescences per flowering stem.
3. Decorative-type inflorescences that are about 6.9 cm in diameter.
4. Attractive dark red purple-colored ray florets.
5. Response time about 64 days.
6. Dark green foliage.
7. Strong and thick flowering stems and peduncles.
8. Good postproduction longevity with inflorescences and foliage maintaining good substance and color for about 14 to 18 days in an interior environment.

Plants of the new Chrysanthemum can be compared to plants of the female parent selection. In side-by-side comparisons conducted in Alva, Fla., plants of the new Chrysanthemum differed primarily from plants of the female parent selection in ray floret coloration as plants of the female parent selection had bronze orange-colored ray florets.

Plants of the new Chrysanthemum can be compared to plants of the male parent selection. In side-by-side comparisons conducted in Alva, Fla., plants of the new Chrysanthemum differed primarily from plants of the male parent selection in the following characteristics:

1. Plants of the new Chrysanthemum were more freely flowering than plants of the male parent selection.
2. Inflorescences of plants of the new Chrysanthemum did not produce pollen whereas inflorescences of plants of the male parent selection produced a moderate amount of pollen.

Plants of the new Chrysanthemum can also be compared to plants of the *Chrysanthemum×morifolium* cultivar Dark Flamenco, not patented. In side-by-side comparisons conducted in Alva, Fla., plants of the new Chrysanthemum differed from plants of the cultivar Dark Flamenco in the following characteristics:

1. Flowering stems of plants of the new Chrysanthemum were taller than flowering stems of plants of the cultivar Dark Flamenco.
2. Plants of the new Chrysanthemum flowered about seven days earlier than plants of the cultivar Dark Flamenco.
3. Plants of the new Chrysanthemum were more freely flowering than plants of the cultivar Dark Flamenco.
4. Plants of the new Chrysanthemum had smaller inflorescences than plants of the cultivar Dark Flamenco.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'True' grown as a natural spray.

The photograph on the second sheet comprises a close-up view of a typical flowering stem of 'True' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse. Two-week old rooted cuttings were planted on Aug. 20, 2002 and received 17 long day/short nights followed by short day/long nights until flowering. Plants were grown as single-stem natural spray cut Chrysanthemums. During the production time, the following environmental conditions were measured: day temperatures, 19 to 24° C.; night temperatures, 4 to 12° C.; and light levels, 3,000 to 5,000 foot-candles. Measurements and numerical values represent averages for six to ten typical flowering stems and were taken about ten weeks after the start of short days.

Botanical classification: *Chrysanthemum×morifolium* cultivar True.

Commercial classification: Decorative-type cut Chrysanthemum.

Parentage:

*Female or seed parent.*—Proprietary *Chrysanthemum×morifolium* seedling selection identified as code number C911, not patented.

*Male or pollen parent.*—Proprietary *Chrysanthemum×morifolium* seedling selection identified as code number D458, not patented.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous decorative-type cut flower that is typically grown as a natural spray.

*Flowering stem description.*—Aspect: Erect. Length: About 122 cm. Diameter (natural spray diameter): About 16 cm. Diameter (base of stem): Thick, about 7 mm. Internode length: About 5.5 cm. Texture: Pubescent; longitudinally ridged. Color: 146A overlain with close to 59A.

*Foliage description.*—Arrangement: Alternate. Length: About 8.3 cm. Width: About 5.8 cm. Apex: Mucronate. Base: Attenuate with truncate tendencies. Margin: Palmately lobed; sinuses divergent to parallel. Texture: Upper and lower surfaces pubescent; smooth and leathery; veins prominent on lower surface. Color: Developing and fully expanded foliage, upper surface: Darker green than 147A. Developing and fully expanded foliage, lower surface: Close to 147B. Venation, upper surface: Close to 147A to 147B. Venation, lower surface: Close to 147B. Petiole: Length: About 1.8 cm. Diameter: About 5 mm. Color: Upper surface: Close to 147B. Lower surface: Close to 147B to 147C.

Flowering description:

*Appearance.*—Decorative-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 64 days later when grown as a natural spray.

*Postproduction longevity.*—In an interior environment, inflorescences and foliage will maintain good color and substance for about 14 to 18 days in an interior environment.

*Quantity of inflorescences.*—Freely flowering habit, about six or seven inflorescences per stem develop.

*Inflorescence size.*—Diameter: About 6.9 cm. Depth (height): About 2.6 cm. Diameter of disc: No disc florets observed. Diameter of receptacle: About 7 mm.

*Inflorescence buds.*—Shape: Oblate. Height: About 8 mm. Diameter: About 9 mm. Color: More green than 147A.

*Ray florets.*—Shape: Elongated oblong; slightly concave to flat. Length: About 3.4 cm. Width: About 7 mm. Corolla tube length: About 2 mm. Apex: Acute to emarginate. Base: Fused. Texture: Smooth, velvety, glabrous; longitudinally ridged. Aspect: Initially upright; when mature, mostly perpendicular to peduncle. Number of ray florets per inflorescence: About 233 arranged in numerous rows. Color: When opening, upper and lower surfaces: Darker than 71A. Fully opened, upper surface: Darker and richer red purple than 59A. Fully opened, lower surface: Darker than 71A.

*Disc florets.*—No disc florets observed.

*Phyllaries.*—Quantity per inflorescence: About 24. Length: About 7.5 mm. Width: About 4 mm. Shape:

Lanceolate to deltoid. Apex: Acute. Base: Truncate. Margin: Entire. Texture, upper surface: Smooth, waxy. Texture, lower surface: Pubescent. Color, upper surface: Close to 146A. Color, lower surface: More green than 147A.

*Peduncles.*—Length: First peduncle: About 18 cm. Fourth peduncle: About 25 cm. Seventh peduncle: About 31 cm. Diameter: Thick, about 4 mm. Angle: About 30° from vertical. Strength: Strong. Texture: Pubescent. Color: 146A.

*Reproductive organs.*—Androecium: No disc florets observed. Gynoecium: Present on ray florets.

*Seed/fruit.*—Seed and fruit production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. and high temperatures high temperatures of 35° C.

It is claimed:

1. A new and distinct cultivar of Chrysanthemum plant named 'True', as illustrated and described.

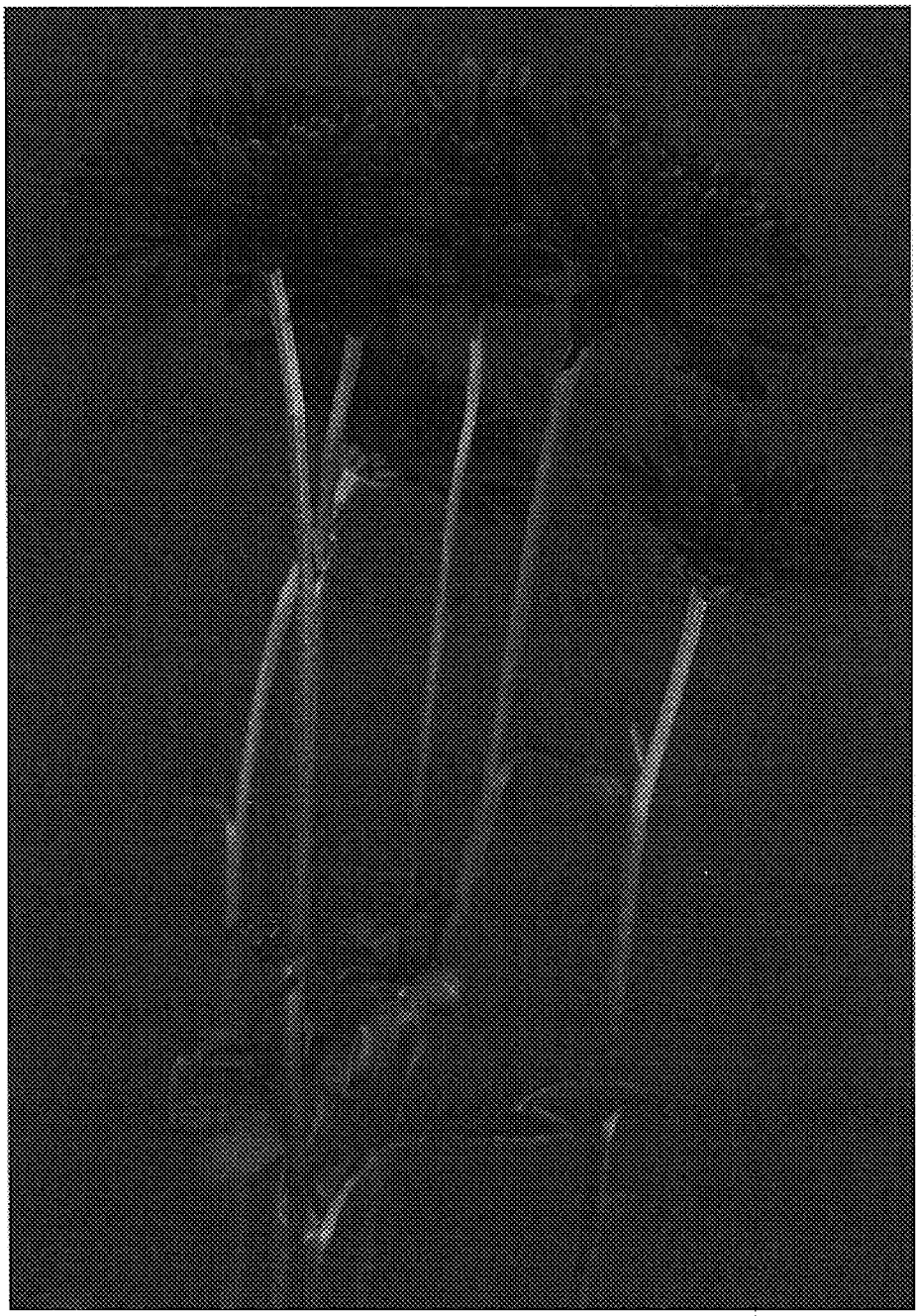

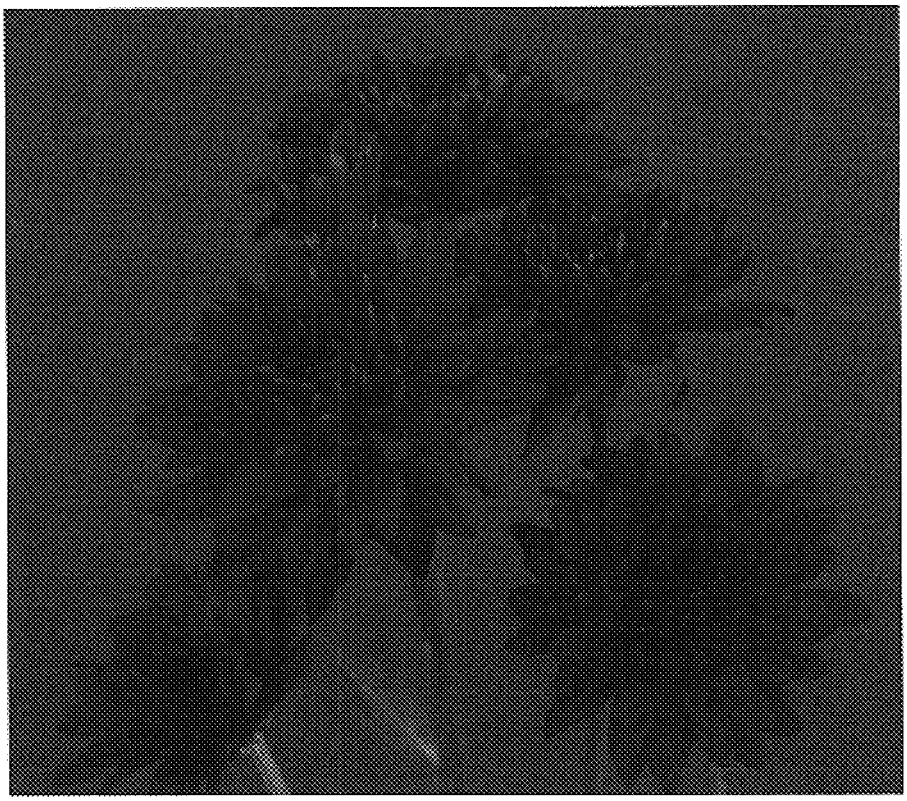

* * * * *